United States Patent [19]

Hirsch et al.

[11] Patent Number: 4,659,730

[45] Date of Patent: Apr. 21, 1987

[54] AROMATASE INHIBITING IMIDAZOLE DERIVATIVES

[75] Inventors: Kenneth S. Hirsch, New Palestine; Charles D. Jones; Harold M. Taylor, both of Indianapolis, Ind.

[73] Assignee: Eli Lilly and Company, Indianapolis, Ind.

[21] Appl. No.: 621,581

[22] Filed: Jun. 18, 1984

[51] Int. Cl.$^4$ ............... A61K 31/415; C07D 405/04; C07D 233/58
[52] U.S. Cl. .................... 514/396; 514/397; 514/399; 548/250; 548/252; 548/255; 548/256; 548/262; 548/336; 548/346
[58] Field of Search .............. 548/336, 341, 346; 424/273 R; 514/397, 399, 396

[56] References Cited

U.S. PATENT DOCUMENTS

| | | | |
|---|---|---|---|
| 3,636,002 | 1/1972 | Godefred | 548/346 |
| 4,115,578 | 9/1978 | Miller et al. | 548/336 |
| 4,144,347 | 3/1979 | Stern | 548/336 |
| 4,235,893 | 11/1980 | Brodie et al. | 260/397.4 |
| 4,278,800 | 7/1981 | Rentzea et al. | 548/262 |
| 4,284,641 | 8/1981 | Thorogood | 548/335 |
| 4,342,775 | 8/1982 | Cozzi et al. | 548/336 |
| 4,468,404 | 8/1984 | Rane et al. | 548/262 |
| 4,503,062 | 3/1985 | Gravestock | 514/383 |
| 4,510,149 | 4/1985 | Cozzi et al. | 548/346 |

FOREIGN PATENT DOCUMENTS

| | | | |
|---|---|---|---|
| 129284 | 10/1980 | Japan | 548/336 |
| 2122997 | 1/1984 | United Kingdom | 548/336 |

OTHER PUBLICATIONS

Siiteri et al., Handbook of Physiology-Endocrinology II, Part I, pp. 615–629 (1977).
Goodman and Gilman's, "The Pharmacological Basis of Therapeutics", 6th Edit., p. 1304 (1980).
Harris, Expl. Cell. Biol., 53, pp. 1–8 (1985).
Brodie et al., Endocrinology, 100, pp. 1684–1695 (1977).
Tseng et al., Obstet and Gyn., 63 (2), pp. 150–154 (1984).
Berkowitz et al., Amer. J. Epidemiology, 121 (2), pp. 238–245 (1985).
Tseng et al., J. Clin. Endocrinology and Metabol. 55 (5), pp. 1029–1031 (1982).
Coombes et al., Lancet, pp. 1237–1239, (Dec. 1, 1984).
Santen et al., Ann. Int. Med., 96, pp. 94–101 (1982).
Barone et al., J. Endocrin. and Metabol., 49, pp. 672–676 (1979).
Cancer Research, 42, (8) (Supplement) (1982).
M. Yamato, et al., "Reactivity of Isocoumarins IV . . .", Chem. Pharm. Bull., 30 (3), 843 (1982).
Chemical Abstracts 95:203829m (1981).
Chemical Abstracts 82:72873c (1975).
Chemical Abstracts 87:4873f (1977).

Primary Examiner—Henry R. Jiles
Assistant Examiner—Kurt G. Briscoe
Attorney, Agent, or Firm—Robert A. Conrad; Leroy Whitaker

[57] ABSTRACT

This invention provides certain azole derivatives and their pharmaceutical formulations. Also provided is a method of inhibiting aromatase and treating or preventing estrogen-dependent diseases in mammals by administering the azole derivatives.

12 Claims, No Drawings

AROMATASE INHIBITING IMIDAZOLE DERIVATIVES

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research,* Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer,* 25, 270 (1971)). Two of the known aromatase inhibitors, testolactone and aminoglutethimide, have shown a beneficial effect in treatment of breast cancer. See *Cancer Research,* supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer,* 49, 2534 (1982). Aromatase inhibitors have not been tried in this disease, but antiestrogens seem to be of benefit. See *Obstet. Gynecol.,* 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.,* 12, 177 (1980).

It is the purpose of this invention to provide novel compounds which inhibit the enzyme aromatase in mammals. The compounds and their pharmaceutical formulations are therefore useful in the treatment or prevention of breast cancer and other estrogen-dependent diseases.

SUMMARY OF THE INVENTION

This invention provides for compounds of the formula

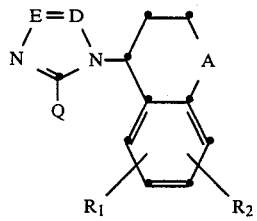

wherein:
Q is hydrogen or methyl;
A is a bond, $-CH_2-$, $-O-$, or $-S-$;
E and D are independently CH or N; and
$R_1$ and $R_2$ are independently hydrogen, $C_1-C_3$ alkyl, halo, trifluoromethyl, or $C_1-C_3$ alkoxy, and pharmaceutically acceptable salts thereof.

This invention also provides a method of inhibiting aromatase in mammals which comprise administering to said mammal an aromatase inhibiting amount of a compound of the above formula. By virtue of their ability to inhibit the enzyme aromatase, the compounds of formula I are useful in the treatment and prevention of estrogen-dependent diseases, especially breast cancer, in mammals.

In addition, this invention also provides for pharmaceutical compositions comprising a compound of the above formulation in combination with a suitable pharmaceutical carrier, diluent, or excipient. Such formulations are especially useful in the treatment of estrogen-dependent diseases in mammals.

DETAILED DESCRIPTION AND PREFERRED EMBODIMENT

The term "$C_1-C_3$ alkoxy" refers to methoxy, ethoxy, propoxy, and isopropoxy. The term "$C_1-C_3$ alkyl" refers to methyl, ethyl, propyl, and isopropyl. The term "halo" refers to fluoro, chloro, bromo, and iodo.

A preferred group of compounds useful in this invention are those wherein Q is hydrogen and (a) A is a bond or $-CH_2-$;

(b) one or both of $R_1$ and $R_2$ is halo, especially chloro, and (c) E and D are both CH.

As will be recognized by those skilled in the art, the compounds of Formula I contain an asymmetric carbon atom. This invention is not limited to any particular isomer but includes the individual enantiomers as well as the racemates of the compounds of Formula I.

The compounds of Formula I can be prepared by any of a number of methods known in the art. A preferred method of preparation is summarized by the following scheme:

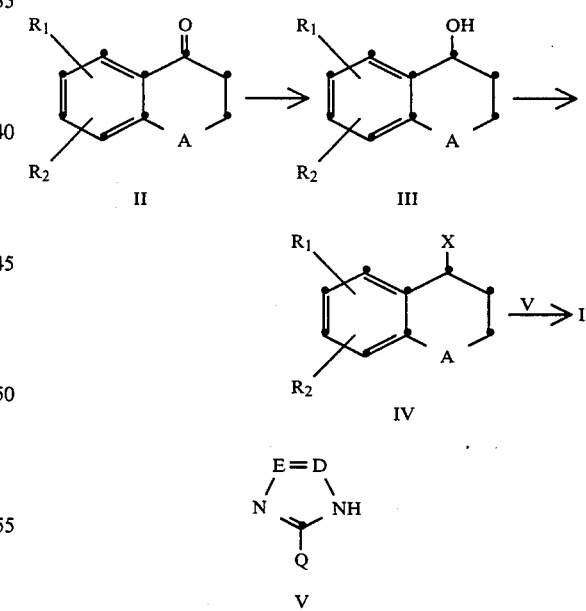

where X is chloro or bromo.

In the above scheme, ketone II is reduced to the alcohol III. This reduction can be accomplished by any of a number of methods known in the art. Preferably, a reducing agent such as sodium borohydride is employed in the presence of a nonreactive solvent, such as water, ethanol, or the like. Usually, 1.5–2.0 moles of the reducing agent are used per mole of II and the reaction is generally carried out at temperatures from about 0° C.

up to about 60° C. Under these conditions, the reaction is generally complete within about 6 hours.

The halo intermediate IV is obtained from intermediate III upon reaction with an appropriate halogenating reagent. The simplest and preferred reaction conditions are those wherein 1.5-2.5 molar equivalents of thionyl chloride or thionyl bromide are reacted with intermediate III in the presence of a nonreactive organic base such as pyridine. The reaction is generally carried out at temperatures of 0°-30° C. and in the presence of a nonreactive solvent such as chloroform. This reaction is generally complete within about 2 hours. Intermediate IV may be isolated by standard methods.

The conversion of intermediate IV to the compound of formula I is accomplished by heating IV with the appropriate azole derivative V in a nonreactive solvent. Generally, a 2-3 molar excess of the azole is employed although other ratios are operative. The reaction is generally carried out in a nonreactive solvent such as acetonitrile, dioxane, dimethylformamide, or the like. The reaction is usually carried out at temperatures from about 20° C. up to the reflux temperature of the reaction mixture. When carried out at the reflux temperature in acetonitrile, the reaction is generally complete within 1-3 days.

When an imidazole derivative is employed as the azole in the reaction with intermediate IV, only the single imidazole derivative of formula I is obtained. When a 1,2,4-triazole derivative is employed as the azole, both the 1- and 4-1,2,4-triazole derivatives are obtained which may be separated by standard methods such as crystallization and high pressure liquid chromatography. When a tetrazole derivative is employed as the azole, both the 1- and 2-tetrazole derivatives are obtained. This mixture may be separated by methods as previously described to produce the 1-tetrazole derivatives of formula I.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- or di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluene-sulfonate, chlorobenzenesulfonate, xylenesulfonate, phenylacetate, phenylpropionate, phenylbutyrate, citrate, lactate, $\beta$-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The starting materials II and azole compounds V as well as some of the intermediate compounds III and IV are commercially available, are known in the literature, or can be prepared by methods known in the art.

In order to more fully illustrate the preparation of the compounds of this invention, the following examples are provided. The examples are illustrative only and are not intended to limit the scope of the invention in any way.

EXAMPLE 1

1-(1,2,3,4-tetrahydro-1-naphthalenyl)-1H-imidazole nitrate

To a solution of 184.1 g of $\alpha$-tetralone in 1 liter of ethanol were added in portions 72 g of sodium borohydride with external ice cooling. After stirring for 2 hours with cooling, the cooling bath was removed and the reaction was heated on a steam bath for 3 hours. Three liters of water were added to the reaction mixture and the mixture was extracted with ether. The ether layer was washed twice with water, dried over magnesium sulfate, and evaporated to dryness. Vacuum distillation of the residue at 3 torr, collecting the fraction at 107°-108° C., provided 165 g of the desired intermediate 1,2,3,4-tetrahydro-1-naphthol.

One hundred grams of 1,2,3,4-tetrahydro-1-naphthol were dissolved in 1 liter of chloroform and 53.9 ml of pyridine. The mixture was cooled with an external ice bath and 98.6 ml of thionyl chloride were added over a 1 hour period. The reaction mixture was stirred an additional 2 hours with cooling, concentrated in vacuo, and the residue taken up in 1 liter of methylene chloride. The methylene chloride solution was washed with water, a 5% sodium bicarbonate solution, water again, dried over sodium sulfate, and evaporated to dryness to provide the desired intermediate 1,2,3,4-tetrahydro-1-chloronaphthalene.

The chloro intermediate from the above paragraph was dissolved in 1 liter of acetonitrile and heated at reflux with 136 g of imidazole for 20 hours. The reaction mixture was concentrated under reduced pressure and the residue was dissolved in methylene chloride. The organic solution was washed with dilute sodium hydroxide solution, water, and then extracted with dilute hydrochloric acid. The hydrochloric acid solution was washed with ether, made basic with sodium hydroxide, and extracted with methylene chloride. The methylene chloride solution was washed with water, dried over sodium sulfate, and evaporated to dryness. The residue was dissolved in 700 ml of ethanol and made acidic with concentrated nitric acid diluted with an equal volume of water. The solution was concentrated to dryness and the residue was crystallized from ethanol/isopropyl ether to provide 71.7 g of the desired title product, m.p. 130°-132° C.

Analysis for $C_{13}H_{15}N_3O_3$: Calc.: C, 59.76; H, 5.79; N, 16.08; Found: C, 59.48; H, 6.04; N, 15.81.

EXAMPLES 2-10

Following the general procedure described in Example 1, the following compounds were prepared from the appropriate starting materials.

2. 1-(2,3-dihydro-1H-inden-1-yl)-1H-imidazole nitrate, m.p. 100°-102° C. 28.2% yield from the chloro intermediate.

Analysis for $C_{12}H_{13}N_3O_3$: Calc.: C, 58.29; H, 5.30; N, 17.00; Found: C, 58.43; H, 5.12; N, 16.99.

3. 1-(4,6-dichloro-2,3-dihydro-1H-inden-1-yl)imidazole nitrate, m.p. 174°-176° C. 28.5% yield from the alcohol intermediate.

Analysis for $C_{12}H_{11}Cl_2N_3O_3$: Calc.: C, 45.59; H, 3.51; N, 13.29; Found: C, 45.69; H, 3.27; N, 13.39.

4. 1-(2,3-dihydro-4,7-dimethoxy-1H-inden-1-yl)-1H-imidazole nitrate, m.p. 148°-150° C. 10.6% yield from the alcohol intermediate.

Analysis for $C_{14}H_{17}N_3O_5$: Calc.: C, 54.72; H, 5.58; N, 13.67; Found: C, 54.61; H, 5.77; N, 13.41.

5. 1-(5,6-dichloro-2,3-dihydro-1H-inden-1-yl)-1H-imidazole nitrate, m.p. 158°-160° C. 25.7% yield from the alcohol intermediate.

Analysis for $C_{12}H_{11}Cl_2N_3O_3$: Calc.: C, 45.59; H, 3.51; N, 13.28; Found: C, 45.82; H, 3.34; N, 13.32.

6. 1-(6-chloro-2,3-dihydro-1H-inden-1-yl)-1H-imidazole nitrate, m.p. 147°-149° C. 4.4% yield from the alcohol intermediate.

Analysis for $C_{12}H_{12}ClN_3O_3$: Calc.: C, 51.17; H, 4.29; N, 14.97; Found: C, 51.02; H, 4.12; N, 14.66.

7. 1-(3,4-dihydro-2H-1-benzothiopyran-4-yl)-1H-imidazole nitrate, m.p. 136°-141° C. 53.6% yield from the chloro intermediate.

Analysis for $C_{12}H_{13}N_3O_3S$: Calc.: C, 51.60; H, 4.69; N, 15.04; Found: C, 51.49; H, 4.66; N, 14.69.

8. 1-(1,2,3,4-tetrahydro-7-methoxy-1-naphthalenyl)-1H-imidazole nitrate, m.p. 136°-138° C. 33.8% yield from the chloro intermediate.

Analysis for $C_{14}H_{15}N_3O_4$: Calc.: C, 57.72; H, 5.88; N, 14.43; Found: C, 57.28; H, 5.81; N, 14.41.

9. 1-(1,2,3,4-tetrahydro-5-methoxy-1-naphthalenyl)-1H-imidazole nitrate, m.p. 142°-144° C. 25.6% yield from the ketone intermediate.

Analysis for $C_{14}H_{17}N_3O_4$: Calc.: C, 57.72; H, 5.88; N, 14.43; Found: C, 57.82; H, 5.62; N, 14.53.

10. 1-(3,4-dihydro-2H-1-benzopyran-4-yl)-1H-imidazole hydrochloride, m.p. 137°-139° C. 30.1% yield from the alcohol intermediate.

Analysis for $C_{12}H_{13}ClN_2O$: Calc.: C, 60.89; H, 5.54; N, 11.84; Found: C, 60.69; H, 5.38; N, 11.96.

The compounds used in this invention are useful in preventing or therapeutically treating estrogen-dependent diseases, including breast cancer, in mammals by virtue of their ability to inhibit the enzyme aromatase. The ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity (EC$_{50}$) when the concentration of substrate (androstenedione) is 0.1 μM. The EC$_{50}$'s of certain of the compounds of formula I are summarized in Table 1.

TABLE 1

| Aromatase Inhibition in the Rat Ovarian Microsome Assay | |
|---|---|
| Compound of Formula I | EC$_{50}$* |
| 1-(3,4-dihydro-2H—1-benzopyran-4-yl)-1H—imidazole hydrochloride | 2.8 |
| 1-(3,4-dihydro-2H—1-benzothiopyran-4-yl)-1H—imidazole nitrate | 1.025 |
| 1-(2,3-dihydro-4,7-dimethoxy-1H—inden-1-yl)-1H—imidazole nitrate | 0.87 |
| 1-(5,6-dichloro-2,3-dihydro-1H—inden-1-yl)-1H—imidazole nitrate | 0.078 |
| 1-(6-chloro-2,3-dihydro-1H—inden-1-yl)-1H—imidazole nitrate | 0.21 |
| 1-(4,6-dichloro-2,3-dihydro-1H—inden-1-yl)-1H—imidazole nitrate | 0.115 |
| 1-(1,2,3,4-tetrahydro-7-methoxy-1-naphthalenyl)-1H—imidazole nitrate | 0.45 |
| 1-(1,2,3,4-tetrahydro-5-methoxy-1-naphthalenyl)-1H—imidazole nitrate | 0.25 |
| 1-(7-chloro-1,2,3,4-tetrahydro-1-naphthalenyl)-1H—imidazole nitrate | 0.10 |
| 1-(4-chloro-2,3-dihydro-1H—inden-1-yl)-1H—imidazole nitrate | 0.68 |
| 1-(1,2,3,4-tetrahydro-1-naphthalenyl)-1H—imidazole nitrate | 0.52 |
| 1-(2,3-dihydro-1H—inden-1-yl)-1H—imidazole nitrate | 0.81 |

*Concentration of compound in μM required to achieve 50% inhibition of aromatase activity when substrate concentration is 0.1 μM.

By virtue of their ability to inhibit the enzyme aromatase, the compounds of this invention are able to inhibit the synthesis of estrogens in mammals, thereby making the compounds useful in the treatment of estrogen-dependent diseases, such as breast cancer. This in vivo activity was demonstrated in the following test system.

ESTROGEN SYNTHESIS INHIBITION IN RATS

Immature female Wistar rats (45-55 grams) were divided into control and test groups of 4-8 animals each. Test compounds were administered for seven days as a component of the diet. Control animals received diet without the test compound. Beginning on the fourth day of the test, all animals treated with the test compound and one half of the control animals were given a subcutaneous injection of 1.0 mg of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl of 3:1 (v/v) saline-ethanol.

After two hours, the animals were killed by decapitation. Uteri were isolated, trimmed of extraneous connective tissue, and weighed. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls.

Ovaries from rats treated with [$^3$H]-testosterone were excised, cleaned of extraneous tissue, and homogenized in 2.5 ml of a 1.0 mM potassium phosphate buffer containing 3.0 mM MgCl$_2$.6H$_2$O, 320 mM sucrose, and 0.25% Triton X-100 (polyethylene glycol p-isooctyl phenyl ether, Rohm and Haas) at pH 6.5. The ovarian steroids were extracted with 1.5 ml of 9:1 (v/v) toluene/ethanol to which had been added 25 to 100 mcg each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography.

Ovarian proteins were precipitated by the addition of 5.0 ml of ethanol to the remaining aqueous phase. After an overnight incubation at 4° C., the samples were centrifuged at 1500×g for 10 minutes. The supernatant was discarded, and the pellet was dissolved in 0.3N potassium hydroxide. Protein was determined according to the method of Bradford, *Analytical Biochemistry*, 72, 248 (1976).

The organic residue from each above extraction was redissolved in 9:1 (v/v) dichloromethane/methanol. The solution of each sample was applied to separate silica gel thin layer chromatography plates which contained a fluorescent indicator. The plates were developed in the first dimension with 160:38:1.5:0.5 (v/v/v/v) dichloromethane/ethyl acetate/methanol/acetic acid to within 3 cm of the top of the plate. After air-drying, the plate was developed in the second dimension with 180:19:1 (v/v/v) dichloromethane/methanol/ammonium hydroxide. The plate was air-dried and viewed under 254 nm UV light.

The visible spots were marked and the plates were sprayed with primulin (0.001% in 4:1 v/v acetone/water) according to the method of Wright, *J. Chromatography*, 59, 220 (1971) which allowed for the identification of additional steroids under 365 nm UV light. The spots were scraped from the plate using a glass wool plugged Pasteur pipet attached to a vacuum line. The steroids were eluted directly into scintillation vials by the addition of 0.2 ml of dichloromethane followed by two washes each of 2.0 ml of methanol. The organic solvent was evaporated and 10.0 ml of scintillation fluid (Beckman Ready Solv-NA) was added to the vials. Samples were analyzed by liquid scintillation spectrometry. Corrections were made based on the recoveries of the [$^{14}$C]-steroid. Steroid concentrations are expressed as femtomoles per milligram protein.

Such pharmaceutical compositions comprise as active ingredient a compound of formula I associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing methods well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, by lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each

TABLE 2

| Effects of a Compound of Formula I on estrogen levels and uterine weight | | | | | | |
|---|---|---|---|---|---|---|
| | | | Mean Uterine | Mean Steroid Concentration** | | |
| Compound | Dose* | Animals | Weight (mg) | estradiol | estrone | estriol |
| 1-(5,6-dichloro-2,3-dihydro-1H—inden-1-yl)-1H—imidazole nitrate | 30 | 4 | 152.5 | 0.71 | 0.21 | 0.46 |
| | 300 | 5 | 103.2+ | 0.35 | 0.17 | 0.49 |
| testosterone-treated control | — | 8 | 140.8 | 0.55 | 0.19 | 0.53 |
| Corn oil control | — | 6 | 59.8+ | — | — | — |

*ppm in feed. 300 ppm corresponds to approximately 30 mg/kg/day; 30 ppm corresponds to approximately 3 mg/kg/day.
**femtomoles per milligram of protein.
+significantly different from testosterone-treated control, $p < 0.05$.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of Formula I.

unit containing a predetermined quantity of active material calculated to produce the desired therapeutic effect, in association with a suitable pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 11

Hard gelatin capsules are prepared using the following ingredients:

|  | per capsule |
|---|---|
| 1-(5-fluoro-6-chloro-2,3-dihydro-1H—inden-1-yl)-1H—imidazole hydrochloride | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 12

Capsules each containing 20 mg of medicament are made as follows:

|  | per capsule |
|---|---|
| 1-(1,2,3,4-tetrahydro-6-iodo-8-ethoxy-1-naphthalenyl)-1H—1,2,4-triazole | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 13

Capsules each containing 100 mg of active ingredient are made as follows:

|  | per capsule |
|---|---|
| 4-(3,4-dihydro-2H—1-benzothiopyran-4-yl)-4H—1,2,4-triazole sulfate | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 14

Tablets each containing 10 mg of active ingredient are made up as follows:

|  | per tablet |
|---|---|
| 1-(3,4-dihydro-7-methyl-8-trifluoromethyl-2H—1-benzopyran-4-yl)-1H—tetrazole | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of a polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 15

A tablet formula is prepared using the ingredients below:

|  | per tablet |
|---|---|
| 1-(5-methyl-6-chloro-2,3-dihydro-1H—inden-1-yl)-1H—tetrazole | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 16

Suppositories each containing 25 mg of active ingredient are made as follows:

|  | per suppository |
|---|---|
| 4-(3,4-dihydro-5,6-dimethoxy-2H—1-benzothiopyran-4-yl)-4H—1,2,4-triazole | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 17

Suspensions each containing 5 mg of medicament per 5 ml dose are made as follows:

|  | per 5 ml of suspension |
| --- | --- |
| 1-(1,2,3,4-tetrahydro-5-fluoro-7-isopropoxy-1-naphthalenyl)-1H—1,2,4-triazole | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 18

An aerosol solution is prepared containing the following components:

|  | Weight % |
| --- | --- |
| 1-(5,6-dichloro-2,3-dihydro-1H—inden-1-yl)-1H—tetrazole | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A method of inhibiting aromatase in a mammal which comprises administering to said mammal an aromatase inhibiting amount of a compound of the formula

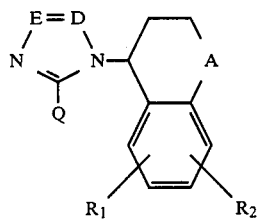

wherein:
Q is hydrogen or methyl,
A is a bond, —CH$_2$—, —O—, or —S—;
E and D are each CH; and
R$_1$ and R$_2$ are each independently hydrogen, C$_1$–C$_3$ alkyl, halo, trifluoromethyl, or C$_1$–C$_3$ alkoxy, or a pharmaceutically acceptable salt thereof.

2. The method according to claim 1 employing a compound wherein A is a bond.

3. The method according to claim 1 employing a compound wherein A is —CH$_2$—.

4. The method according to claim 2 employing 1-5,6-dichloro-2,3-dihydro-1H-inden-1-yl)-1H-imidazole or a pharmaceutically acceptable salt thereof.

5. A method of treating estrogen-dependent diseases in a mammal which comprises administering to said mammal an effective amount of a compound of the formula

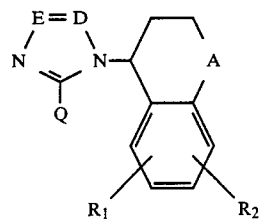

wherein:
Q is hydrogen or methyl,
A is a bond, —CH$_2$—, —O—, or —S—;
E and D are each CH; and
R$_1$ and R$_2$ are each independently hydrogen, C$_1$–C$_3$ alkyl, halo, trifluoromethyl, or C$_1$–C$_3$ alkoxy, or a pharmaceutically acceptable salt thereof.

6. The method according to claim 5 employing a compound wherein A is a bond.

7. The method according to claim 6 employing a compound wherein R$_1$ is chloro.

8. The method according to claim 7 employing 1-(5,6-dichloro-2,3-dihydro-1H-inden-1-yl)-1H-imidazole or a pharmaceutically acceptable salt thereof.

9. The method according to claim 5 wherein the estrogen-dependent disease is breast cancer.

10. The method according to claim 9 employing a compound wherein A is a bond.

11. The method according to claim 10 employing a compound wherein R$_1$ and R$_2$ are each chloro.

12. The method according to claim 11 employing 1-(5,6-dichloro-2,3-dihydro-1H-inden-1-yl)-1H-imidazole or a pharmaceutically acceptable salt thereof.

* * * * *

UNITED STATES PATENT AND TRADEMARK OFFICE
CERTIFICATE OF CORRECTION

PATENT NO. : 4,659,730

DATED : April 21, 1987

INVENTOR(S) : Kenneth S. Hirsch et al.

It is certified that error appears in the above—identified patent and that said Letters Patent is hereby corrected as shown below:

On the title page, under "Inventors", the third line "both of Indianapolis, Ind." should read --both of Indianapolis; Robert D. Dillard, Zionsville, Ind.--.

Signed and Sealed this

Twenty-fifth Day of August, 1987

Attest:

DONALD J. QUIGG

*Attesting Officer*  *Commissioner of Patents and Trademarks*